United States Patent [19]

Rabbani

[11] 4,139,346

[45] Feb. 13, 1979

[54] NUCLEIC ACID AND PROTEIN BINDING PAPER

[75] Inventor: Elazar S. Rabbani, New York, N.Y.

[73] Assignee: Enzo Bio Chem Incorporated, New York, N.Y.

[21] Appl. No.: 855,330

[22] Filed: Nov. 28, 1977

[51] Int. Cl.$^2$ .................... G01N 31/22; G01N 33/16
[52] U.S. Cl. .................................. 422/56; 23/230 B; 23/230.3
[58] Field of Search ............ 23/253 TP, 230 B, 230.3, 23/230.6; 424/1; 252/301.1 R

[56]  References Cited
U.S. PATENT DOCUMENTS 4,069,352  1/1978  Parsons, Jr. .................... 23/253 TP

OTHER PUBLICATIONS

J. Applied Chem., vol. 16, pp. 351–355 (1943).

Primary Examiner—R.E. Serwin
Attorney, Agent, or Firm—Fitzpatrick, Cella, Harper & Scinto

[57] ABSTRACT

A paper modified with aminobenzyloxymethyl groups for binding, upon activation, nucleic acid residues or proteins. The immobilized residues are analyzed by hybridization with isotope-labeled probes.

14 Claims, No Drawings

NUCLEIC ACID AND PROTEIN BINDING PAPER

BACKGROUND OF THE INVENTION

1. Field of the Invention

The present invention relates to a chemically modified paper adapted to immobilize nucleic acid residues and proteins and a method for producing and utilizing the same.

2. Description of the Prior Art

Living cells contain nucleoproteins which are proteins combined with natural polymers, called nucleic acids. Nucleic acids have a long chain backbone attached to which are various groups, which by their nature and sequence, characterize each nucleic acid. The backbone of protein is a polyamide chain, whereas the backbone of the nucleic acid molecule is a polyester chain; a polynucleotide chain. The ester is derived from phosphoric acid and sugar.

The sugar is D-ribose for the nucleic acids known as ribonucleic acids (RNA) and the sugar is D-2-deoxyribose in the group known as deoxyribonucleic acids (DNA). Attached to each sugar, through a beta-linkage is one of a number of heterocyclic bases. A base-sugar unit is a nucleoside; a base-sugar-phosphoric unit is a nucleotide.

The bases in DNA are adenine and guanine, which contain the purine ring system; and cytosine, thymine and 5-methylcytosine, which contain the pyrimidine ring system. RNA contains adenine, guanine, cytosine and uracil. The proportions of these bases and their sequence along the polynucleotide chain differ from one kind of nucleic acid to another.

DNA consists of two polynucleotide chains wound about each other to form a double helix. The helixes are bound to each other at intervals by hydrogen bonding between the bases. The nucleic acids, as DNA, control heredity on the molecular level. The genetic code is stored as the sequence of bases along the polynucleotide chain, consisting of permutations of adenine (A), guanine (G), thymine (T) and cystosine (C). For RNA, uracil (U) is substituted for thymine (T).

In most entities genetic information is channeled from DNA into messenger RNA (mRNA) and then translated with the help of transfer RNA (tRNA) into polypeptides. The transfer of information from DNA to mRNA is known as transcription and occurs when a mRNA strand complements a part of one DNA strand. Transfer RNA brings specific amino acids to a ribosome - associated, mRNA template, holds them there while the amino acids are joined to a polypeptide structure and is then released by enzymatic acid from the polypeptide chain. RNA is also found in ribosome particles which consist of ribosomal RNA (rRNA) and protein. Both tRNA and rRNA have double-stranded regions as a result of folding back onto itself.

As employed herein the term "residue" includes an entire strand or chain and parts of said strand or chain of nucleic acids, such as RNA or DNA. The complementary binding of mRNA to a strand of a cell's DNA was demonstrated by "hybridization" tests in 1961. In conventional hybridization a residue of a nucleic acid, as mRNA residue, is separated and pulse labeled with a radioactive isotope, such as Phosphorous 32, ($P^{32}$). The labeled residue is incubated with a heat-denatured (single stranded), nucleic acid, as DNA. When the DNA, for example, is from the same species as the RNA, the mRNA will hybridize with the complementary DNA strand on cooling. The non-hybridized RNA can then be destroyed by RNAase treatment, a conventional treatment, and the RNA-DNA hybrid, identifiable by the presence of $P^{32}$ labeled RNA, and other tests is recovered. Hybrids are formed only when homologous DNA and RNA (having complementary bases) are employed. Similarly, labeled tRNA and rRNA from a given species hybridizes only with their homologous DNA.

In conventional hybridization testing, DNA only was immobilized on a solid matrix. For example, DNA was coupled to acetylated, phosphorylated cellulose in a chromatography column. The phosphate groups on the cellulose acetate combined with the glycosylic hydroxyls of the (sugar) deoxyribose of DNA. Another method employed agar or gel to trap denaturated DNA. Others proposed to hydrogen bond DNA residues to nitrocellulose membranes. Still others attempted to link DNA to cellulose using water-soluble carbodiimide or to link DNA to agarose, activated with cyanogen bromide.

Such prior immobilization of DNA residues has not proved entirely satisfactory. In all prior attempts to hybridize, DNA was immobilized on a matrix. RNA has not been successfully immobilized, so that a labeled DNA residue could act as a probe. This is a serious defect. Further, the relatively large amount of necessary support matrix prohibited sensitive analytical hybridization studies.

In addition, the proposed nitrocellulose matrix is a relatively unstable substrate for DNA, since only a hydrogen bond, not a covalent bond, is formed. Further, short chains or residues of DNA, when applied to nitrocellulose, are too unstable for successful hybridization. Therefore, one could not use desirable, highly fractionated DNA chains for hybridization, only relatively long chains of DNA.

Therefore, there exists a long felt need to provide a compact matrix for covalently immobilizing both long and short residues of both DNA and RNA, as well as proteins, to allow small fractions of nucleic acids or proteins to be sensitively analyzed with labeled probes. In Volume 16, *J. Applied Chem.* pp. 351–355 (1943) cotton fabric, not paper, was impregnated with pyridine salts of chloromethyl ethers. Upon suitable reduction and activation, the cotton fabric was dyed by coupling 2-naphthol with the diazotized fabric. Cotton fabric is not a suitable substrate for hybridization, as a column containing such fabric would have to be employed. Further, there is no teaching in the article of immobilizing nucleic acids or proteins.

For the purpose of this application reverse hybridization includes immobilizing RNA on a thin matrix and probing with labeled DNA.

SUMMARY OF THE INVENTION

It is therefore, an object of the present invention to provide a compact substrate to selectively immobilize nucleic acids, as RNA or DNA and proteins, to allow hybridization with a homologous labeled probe.

It is another object to provide a flat matrix to covalently bond either DNA or RNA in large or small chain residues for sensitive hybridizations or reverse hybridizations.

The above and other objects are met by employing a modified cellulosic paper substituted with m-aminobenzyloxymethyl groups. The amino moieties in the groups are activated prior to use by conventional diazotization techniques. The heterocyclic bases on nucleic acids and nitrogenous heterocyclic bases on proteins form covalent bonds with the phenyl ring containing the diazo group. Short and long chain nucleic acids and proteins are immobilized to the paper for labeled probing with complementary residues. Thin sheets of paper as the substrate allow the use of minor amounts of residues for highly sensitive hybridizations or reverse hybridizations.

To prepare the modified paper of the invention a cellulosic paper, preferably as a thin sheet or web, is treated with 1[(meta-nitrobenzyloxy) methyl] pyridinium chloride to introduce covalently bonded meta nitrobenzyloxymethyl groups to the cellulosic backbone. The nitro moiety on the groups is then reduced with appropriate reducing agents to an amino substituent. The so-modified paper is storage stable and readily activated by diazotization.

DESCRIPTION OF PREFERRED EMBODIMENTS

The modified paper of the invention is derived generally, from a sheet or continuous web of cellulosic fibers. Preferably, a thin sheet of paper is employed, particularly conventional filter paper. Other readily adapted natural or synthetic substrates adapted to be substituted with groups which are convertible to diazo groups for bonding with nucleic acids and proteins according to the invention may also be employed.

To form the modified paper of the invention 1-[(meta-nitrobenzyloxy) methyl] pyridinium chloride is preferably employed. Preparation of this compound is disclosed in *J. Applied Chem* (U.S.S.R.), 16, 351–355 (1943) and this disclosure is incorporated by reference. Other suitable compounds adapted to provide the diazotizable aromatic functional group can also be employed. Salts of other halogens, acids or other anions may be employed in place of the chloride anion, provided they do not interfere with the preparation and activation of the diazo group. Other pyridine salts of chloromethyl ethers adapted to bond with paper and yield diazotizable groups can be utilized.

An example of a preferred technique to prepare the modified cellulosic paper is as follows:

PREPARATION EXAMPLE I

A sheet of filter paper (20 × 20 cm) was soaked with a 10% solution of 1-[(m-nitrobenzyloxy)methyl] pyridinium chloride (NBPC) in 0.2 M solution of sodium acetate in a pyrex glass tray. The paper was dried at 60° and then heated for 30 minutes at 130°. The paper was washed with water and then benzene and dried at room temperature. The nitrobenzyloxymethyl paper was reduced to aminobenzyloxymethyl paper (ENZOBOND$^{TM}$ paper) by treating with 20% sodium dithionite (W/V) for 30 minutes at 60° C. The paper was then washed with water and 5 N acetic acid and again with water. The paper was dried at room temperature and stored, sealed at 4° C.

It will be apparent that other reducing agents in addition to sodium dithionate may be employed, such as sodium hyposulfite, to convert the nitro groups to amino groups.

To prepare the meta-nitrobenzyloxy methyl pyridinium chloride, polyoxymethylene is admixed with m-nitrobenzyl alcohol and allowed to react. The resulting m-nitrobenzyl chloromethyl ether is treated with pyridine to achieve the desired product.

In order to activate the ENZOBOND$^{TM}$ paper (aminobenzyloxymethyl paper) prior to reaction with nucleic acid residues or proteins, a conventional diazotizing reaction employing nitrous acid or acidic solutions of sodium nitrate is conducted. Typically, the reaction is carried out at low temperatures, below 10° C to prevent decomposition. A preferred preparation example is as follows:

PREPARATION EXAMPLE II

Activation (Diazotization) of Modified Paper

Prior to reaction with nucleic acid residues ENZOBOND$^{TM}$ paper (20 × 20 cm) prepared according to Preparation Example I was converted to the activated form (diazobenzyloxymethyl form) by treatment with a solution containing 120 ml of 1.2 M HCl and 3.2 ml of a freshly prepared solution of NaNO$_2$ (10 mg/ml) for 30 min at 4° C. The solution was checked for free HNO$_2$ using starch-iodide paper, which turns black in the presence of free HNO$_2$. After 30 minutes, the activated paper was washed five times for five minutes each with 100 ml of cold water and then twice for 10 minutes with ice cold sodium borate buffer, 0.1 M, pH 8. Upon washing, the paper turns bright yellow. The activated paper should be kept cold until transfers begin, preferably no more than 15 minutes later. Activated paper has the capacity to couple 16 to 24 micrograms of single-stranded nucleic acid per cm$^2$ of surface area.

Diagramatically, the reaction sequence for preparation of the modified paper and its subsequent activation is as follows:

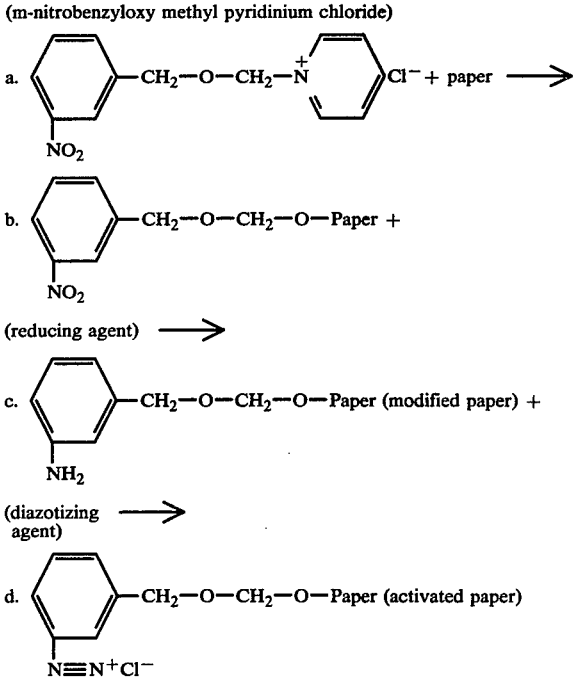

The activated paper can thereafter react with proteins and nucleic acid residues, as RNA or DNA residues, to form a stable covalent bond with the aromatic nitrogenous bases on the nucleic acid polyester backbone. It has been postulated that the present reaction mechanism is analogous to the Gomberg-Bachmann reaction whereby an aromatic diazonium chloride is arylated under basic conditions at low temperatures. Arylation takes place chiefly para, or if this position is blocked, ortho to most substituents. In the present invention the following reaction occurs for nucleic acids and proteins:

e.

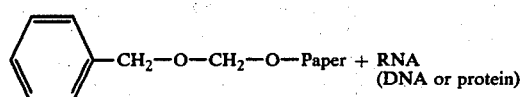

f.

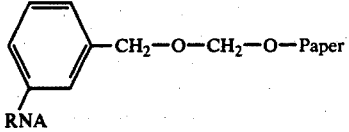

The by-products of this reaction are nitrogen gas, water and halide. The nucleic acid residue is theorized to be bound to the benzyl ring through the pyrimidine or purine ring of the base.

In general, RNA present in a given solution may be immobilized with activated paper by blotting the activated paper between filter papers. Thereafter, RNA, which has been contacted with a borate or other buffer at a basic pH, preferably about pH 8, is placed in contact with the activated paper at a low temperature, preferably below 10° C, most preferably at 4° C. The RNA is allowed to contact the activated paper for from 1-12 hours.

DNA is bound to activated paper in a similar fashion. Denatured DNA residues, for example, with as little as 100 bases on the polyester residue or less, can be immobilized. In general, DNA under conventional denaturing conditions is buffered by means of a borate buffer or the like to a basic pH, preferably about 8 in an 80% by weight dimethylsulfoxide solution. Again, the DNA solution is contacted with activated paper at low temperatures, for from 1-12 hours.

Proteins are immobilized in a similar fashion in solutions at a basic pH in the cold with contact periods ranging to a few days or more.

An important application of modified paper is in gel-transfer-hybridization techniques for detecting and determining the size of specific RNA molecules. The inventive technique involves the transfer of electrophoretically separated RNA species from agarose gels onto modified paper of the invention and by hybridizing the RNA on the paper to suitable $^{32}$p-labeled DNA probes. The procedure for preparing isotope labeled probes is well known and understood by the art.

Similarly, the technique for electrophoretically separating RNA species from agarose gels is well documented in the literature, such as in the Southern article in *J. Mol. Biol.* (1975) 98, pp. 503-517 and articles referenced therein.

Hybridization of immobilized nucleic acid residues is accomplished with nucleic acid residue probes labeled with isotopes as $P^{32}$ by conventional techniques, as disclosed by Denhardt (1966) *Biochem. Biophys. Res. Common.* 23, p. 641.

The following illustrative examples are representative of certain specific embodiments of the invention.

EXAMPLE I

In order to immobilize RNA residues, activated paper prepared according to Preparation Example II is blotted between filter papers. An RNA residue is placed in a 0.1 M borate buffer at a pH 8. The resulting solution is contacted with the activated paper at 4° C for 12 hours. The immobilized RNA is detected and analyzed by a labeled complementary $p^{32}$ DNA residue.

EXAMPLE II

In order to immobilize DNA residues, activated paper is prepared according to Preparation Example II and blotted between filter paper. Denatured DNA residues having under 100 bases are dissolved in an 80% dimethylsulfoxide solution containing 0.1 M borate buffer at a pH of 8. The resulting solution is contacted with the activated paper for 12 hours at 4° C. The activated paper containing immobilized DNA residues is probed with complementary $p^{32}$ labeled RNA residues.

EXAMPLE III

In order to immobilize proteins, activated paper is prepared according to Preparation Example II and blotted between sheets of filter paper. Proteins containing histidine bases are dissolved in a 0.1 M borate buffer at a pH of 8 at 4° C. The protein solution is contacted with the activated paper for 48 hours at temperatures below 10° C.

EXAMPLE IV

To illustrate the transfer of RNA from an agarose gel to activated paper a gel containing RNA residue is placed on 2 sheets of Whatman 3MM paper saturated with 50 mM sodium borate buffer pH 8.0. A strip of activated paper prepared according to Preparation Example II is saturated in this buffer and placed directly on the gel, using plexiglass strips to prevent the activated paper from contacting the underlying 3MM paper at the sides of the gel. The activated paper is then covered with 2 layers of dry 3MM paper, several layers of paper towels and finally a plexiglass weight. The borate buffer is allowed to blot through until the towels are soaked. After 4 changes of towels the assembly is left overnight. It is essential to time the conversion of modified paper to activated diazotized paper so that the latter can be placed on the gel within a few minutes after the final gel washes are complete.

EXAMPLE V

In order to further illustrate hybridization of immobilized nucleic acid residues, the paper containing immobilized RNA residues prepared according to Example III was pre-treated with hybridization buffer for from 4 to 24 hours to hydrolyze any remaining diazo groups and block any other non-specific sites on the paper which might bind an isotope labeled complementary probe. The hydridization buffer was prepared by mixing 50% by weight formamide, 0.75 M solution sodium chloride, 0.075 M solution of sodium citrate containing 0.02% W/V each of bovine serum albumin, ficoll and polyvinylpyrrolidone, 1.0 to 2.5 mg/ml sonicated (ultrasonic treated), denatured non-homologous DNA and 1% W/V glycine. Thereafter, the treated paper containing immobilized RNA was probed with homologous p³² labeled DNA.

It will be apparent to those skilled in the art that the modified cellulose paper of the invention can be employed for RNA-DNA, RNA-RNA, DNA-RNA or DNA-DNA hybridization and for gel - transfer-hybridizations for isolating, detecting and determining the size of specific genes (DNA molecules) or messenger RNA molecules or proteins. Both RNA immobilized paper and DNA immobilized paper can be interacted with specific proteins, and likewise protein bound paper can be interacted with specific RNA or DNA probes.

The aforesaid invention is not to be limited except as set forth in the following claims.

Wherefore, I claim:

1. A modified cellulosic paper comprising a sheet or continuous web of cellulosic fibers substituted with meta-aminobenzyloxymethyl groups, said modified paper adapted to be activated by diazotization for covalent binding thereto of nucleic acid residues, proteins or mixtures thereof.

2. The modified paper of claim 1 substituted with diazotized meta-aminobenzyloxymethyl groups.

3. The paper of claim 1 covalently bonded with nucleic acid residues.

4. The paper of claim 3 wherein said nucleic acid residues are denatured DNA residues.

5. The paper of claim 3 wherein said nucleic acid residues are RNA residues.

6. The paper of claim 1 covalently bonded with protein chains.

7. The paper of claim 4 hybridized with isotopelabeled RNA residues.

8. The paper of claim 5 hybridized with isotopelabeled DNA residues.

9. A process for preparing a modified cellulosic paper adapted for activation by diazotization and subsequent covalent bonding thereto by nucleic acid residues, proteins or mixtures thereof comprising treating a sheet or continuous web of cellulosic fibers with 1-[(meta-nitrobenzyloxy) methyl] pyridinium chloride and thereafter recovering a meta-nitrobenzyloxymethyl substituted sheet or web, then reducing said nitrobenzyloxymethyl substituents to aminobenzyloxymethyl substituents and thereafter recovering said modified cellulosic paper.

10. The process of claim 9 including diazotizing the amino moieties of said aminobenzyloxymethyl substituents to form a diazotized paper and thereafter contacting said diazotized paper with a nucleic acid residue or a protein chaine to immobilize said chain or residue.

11. The process of claim 9 wherein said nucleic acid residue is a DNA or RNA residue.

12. The process of claim 11 wherein said DNA or RNA residue is hybridized to a corresponding isotope labeled RNA or DNA probe residue to detect the size and identity of the immobilized residue.

13. A modified cellulose paper substituted with diazotizable functional groups for covalently binding nucleic acid residues, proteins or mixtures thereof.

14. A process for preparing a modified cellulose paper adapted for activation by diazotization and subsequent covalent bonding thereto by nucleic acid residues, proteins or mixtures thereof comprising treating a cellulosic paper with a reagent to form covalently bonded substituents having a meta-nitro substituted aryl group, reducing the nitro groups to amino groups and recovering the modified paper.

* * * * *

UNITED STATES PATENT AND TRADEMARK OFFICE
CERTIFICATE OF CORRECTION

PATENT NO. : 4,139,346
DATED : February 13, 1979
INVENTOR(S) : Elazar S. Rabbani It is certified that error appears in the above–identified patent and that said Letters Patent are hereby corrected as shown below:

Claim 10, line 18, "chaine" should be --chain--.

Signed and Sealed this

Eighth Day of May 1979

[SEAL]

Attest:

RUTH C. MASON
Attesting Officer

DONALD W. BANNER
Commissioner of Patents and Trademarks